United States Patent [19]
Cliffe et al.

[11] Patent Number: 5,763,460
[45] Date of Patent: Jun. 9, 1998

[54] N-(PIPERIDINYL-1-ALKYL)-SUBSTITUTED CYCLOHEXANE CARBOXYLIC ACID AMIDES AS 5-HT1A RECEPTOR ANTAGONISTS

[75] Inventors: Ian Anthony Cliffe, Slough; Terence James Ward, Reading; Chapman White Alan, Staines, all of England; Antony Ashwell Mark, Plainsboro, N.J.; Bernhard Baudy Reinhardt, Yardley, Pa.

[73] Assignees: John Wyeth & Brother Limited; American Home Products Corporation, both of Madison, N.J.

[21] Appl. No.: 583,103

[22] PCT Filed: Jul. 12, 1994

[86] PCT No.: PCT/GB94/01507

§ 371 Date: Jan. 16, 1996

§ 102(e) Date: Jan. 16, 1996

[87] PCT Pub. No.: WO95/02592

PCT Pub. Date: Jan. 26, 1995

[30] Foreign Application Priority Data

Jul. 16, 1993 [GB] United Kingdom ............ 9314758

[51] Int. Cl.⁶ .......... A61K 31/445; A61K 31/55; C07D 401/12; C07D 405/14

[52] U.S. Cl. .......... 514/326; 514/183; 514/212; 514/331; 514/339; 514/357; 514/428; 540/596; 540/597; 540/610; 544/130; 544/131; 544/360; 544/364; 546/193; 546/194; 546/205; 546/207; 546/208; 546/233; 546/277.7; 546/282.4; 546/268.1; 546/279.1; 546/337; 548/568; 548/950

[58] Field of Search .......... 540/596, 597, 540/610; 544/130, 131, 360, 364; 546/193, 194, 205, 207, 208, 233, 234, 277.7, 282.4, 268.1, 279.1, 337; 548/568, 950; 514/183, 212, 326, 331, 339, 357, 428

[56] References Cited

U.S. PATENT DOCUMENTS 5,143,916 9/1992 Lavielle et al. ............ 514/255
5,169,845 12/1992 Cliffe et al. ............ 514/212
5,177,078 1/1993 Ward et al. ............ 514/253
5,250,544 10/1993 Lavielle et al. ............ 514/319
5,369,103 11/1994 Cliffe et al. ............ 514/211
5,472,966 12/1995 Sloan et al. ............ 514/255
5,525,600 6/1996 Baudy ............ 514/212
5,585,374 12/1996 Cliffe et al. ............ 514/212

FOREIGN PATENT DOCUMENTS 479546 4/1992 European Pat. Off. .
481742 4/1992 European Pat. Off. .
512755 11/1992 European Pat. Off. .
9206960 4/1992 WIPO .
9403444 2/1994 WIPO .

OTHER PUBLICATIONS

Hiltmann et al. "2-Acylamino pyridine derivatives with morphine agonistic and morphine antagonistic properties" CA 81:37463b, 1974.

Primary Examiner—Ceila Chang
Attorney, Agent, or Firm—Arthur G. Seifert

[57] ABSTRACT $$R-\begin{array}{c}(CH_2)_a\\ \\(CH_2)_b\end{array}N-A-N\begin{array}{c}R^1\\ \\COR^2\end{array} \quad (I)$$

Compounds of formula (I) and the pharmaceutically acceptable acid addition salts thereof are 5-HT$_{1A}$ binding agents and may be used, for example, as anxiolytics. In the formula a and b each represents 0, 1, 2 or 3 such that the sum of a+b is 0, 1, 2 or 3, the dotted line represents an optional double bond which may be present in the ring, provided that a is at least 1, A is an alkylene chain of 1 or 2 carbon atoms optionally substituted by one or more lower alkyl groups, R is a mono or bicyclic aryl or heteroaryl radical with the proviso that R is not an unsubstituted phenyl group, $R^1$ is a mono or bicyclic heteroaryl radical, and $R^2$ is cycloalkyl or cycloalkenyl.

15 Claims, No Drawings

N-(PIPERIDINYL-1-ALKYL)-SUBSTITUTED CYCLOHEXANE CARBOXYLIC ACID AMIDES AS 5-HT1A RECEPTOR ANTAGONISTS

This application is a 371 of PCT/GB94/01501 filed Jul. 12, 1994. This invention relates to novel heterocyclic derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

Von R. Hiltmann et al in Arzneim-Forsch. (Drug Res.), 1974, 24, 584–600 discloses certain 2-acylaminopyridine derivatives having morphine agonistic or antagonistic properties.

The novel compounds of the invention are those of general formula

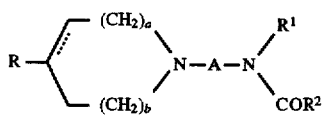

and the pharmaceutically acceptable acid addition salts thereof.

In formula I a and b each represent 0,1,2 or 3 such that the sum of a +b is 0,1,2 or 3, the dotted line represents an optional double bond which may be present in the ring, provided that a is at least 1, A is an alkylene chain of 1 or 2 carbon atoms optionally substituted by one or more lower alkyl groups, R is a mono or bicyclic aryl or heteroaryl radical with the proviso that R is not an unsubstituted phenyl group, $R^1$ is a mono or bicyclic heteroaryl radical.

$R^2$ is cycloalkyl or cycloalkenyl.

The term "lower" as used herein means that the radical referred to contains 1 to 6 carbon atoms. Preferably such radicals contain 1 to 4 carbon atoms. Examples of "lower alkyl" radicals are methyl, ethyl, propyl, isopropyl, butyl, tert.-butyl, pentyl and isopentyl.

A cycloalkyl or cycloalkenyl group can contain 3 to 12 (e.g. 3 to 8) carbon atoms. Preferably a cycloalkyl group is cyclopentyl, cyclohexyl or cycloheptyl, most preferably cyclohexyl. Preferably a cycloalkenyl group is cyclohex-3-enyl.

When used herein "aryl" means an aromatic radical having 6 to 12 carbon atoms (e.g. phenyl or naphthyl) which optionally may be substituted by one or more substituents. Preferred substituents are lower alkyl, lower alkenyl, lower alkynyl, lower alkoxy (e.g. methoxy, ethoxy, propoxy, butoxy), hydroxy, halogen (e.g. chlorine), halo(lower)alkyl (e.g. trifluoromethyl), nitro, nitrile, carbamoyl, (lower) alkylcarbamoyl, di(lower)alkyl carbamoyl, (lower) alkylcarbonyl, (lower)alkoxycarbonyl, amino, (lower) alkylamino and di(lower)alkylamino.

Two substituents on the aromatic ring may be connected together to form another ring system. For example R may be a bicyclic oxygen-containing radical of the formula

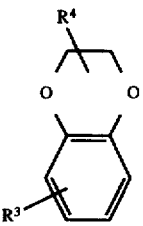

wherein $R^3$ represents hydrogen or one or more same or different substituents selected from lower alkyl, halogen, hydroxy, (lower)alkoxy, hydroxy(lower)alkyl, (lower) alkoxy(lower alkyl), lower alkanoyloxy(lower alkyl), (lower)alkylcarbonyl, (lower)alkylcarbonyl-(lower)alkyl, (lower)alkylcarbonylamino, amino, (lower)alkylamino or di(lower)alkylamino and the heterocyclic ring containing the oxygen atom contains a total of 5 to 7 ring members, said heterocyclic ring being saturated or unsaturated, being optionally substituted (e.g. by one or more substituents $R^4$ where $R^4$ has the meaning given for $R^3$ above) and optionally containing one or more hetero ring members (e.g. —O—, —S—, —SO$_2$— or —NR$^5$— where $R^5$ is hydrogen or lower alkyl) in addition to the oxygen atom illustrated A preferred example of such a bicyclic oxygen radical is a radical of the formula where $R^3$ and $R^4$ are as defined above; preferably $R^3$ and $R^4$ are both hydrogen.

The term "heteroaryl" refers to an aromatic radical containing one or more (e.g. 1, 2 or 3) hetero ring atoms (e.g. oxygen, nitrogen, sulphur) and which may be optionally substituted by one or more substituents. Examples of suitable substituents are given above in connection with "aryl" radicals. The heteroaryl radical may, for example, contain 5 to 10 ring atoms. The heteroaryl radical may be mono- or bicyclic. A monocyclic radical may, for example, contain 5 to 7 ring atoms. Preferably the hetero ring contains a nitrogen atom with or without one or more further hetero atoms. Examples of heteroaryl groups include, for example, pyridinyl, pyrimidinyl, pyrazinyl, quinolinyl, isoquinolinyl and indolyl each of which may be optionally substituted as mentioned above.

A particularly preferred $R^1$ group is pyridinyl, particularly 2-pyridyl.

When R is a heteroaryl radical it is preferably optionally substituted pyrimidyl (particularly 2-pyrimidyl), 1,2-benzisothiazolyl, indolyl [particularly indol-3-yl (which may be optionally substituted e.g. by (lower)alkoxy for example in the 5-position) and indol-5-yl (which may be optionally substituted e.g. by (lower)alkylcarbonyl for example in the 2-position)] or thiophenyl, [particularly thiophen-2-yl which optionally may be substituted for example in the 3-position by one of the preferred substituents mentioned above and the sulphoxide of such thiophenyl radical]

Preferred compounds of formula I have the following characteristics either singly or in any possible combination:

(a) the ring system

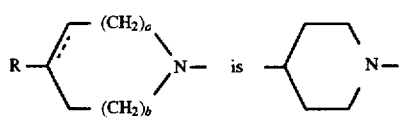 is 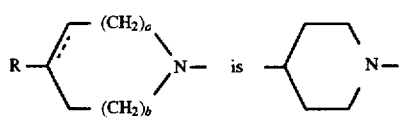

(b) (i) R is a phenyl radical which is substituted by one or more of the substituents mentioned above. Preferably the substituent is in the ortho position. A particularly preferred R group is 2-(lower)alkoxyphenyl e.g. 2-methoxyphenyl. (ii) R is a indolyl radical which may be substituted by one or more of the substituents mentioned above.

(c) A is —CH$_2$—, —CH$_2$CH$_2$— or —CH$_2$—CH(CH$_3$)—.

(d) R$^1$ is 2-pyridyl.

(e) R$^2$ is cyclohexyl.

A particularly preferred compound is (R)-N-(2-(1-(4-(2-methoxyphenyl)piperidino))propyl)-N-(2-pyridyl)cyclohexanecarboxamide.

A particular class of compounds provided by the invention are the thiophen-2-yl derivatives of formula

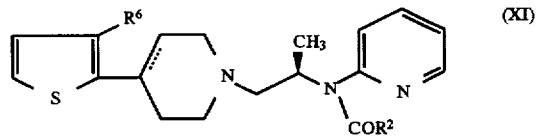 (XI)

wherein the dotted line and R$^2$ are as defined above R$^6$ is hydrogen, lower alkyl, lower alkenyl, lower alkynyl, nitrile, hydroxy, (lower)alkoxy, (lower)alkylcarbonyl, (lower) alkoxycarbonyl, carbamoyl, (lower)alkylcarbamoyl, di(lower)alkylcarbamoyl, halo(lower)alkyl or halogen or the sulphoxides thereof of formula

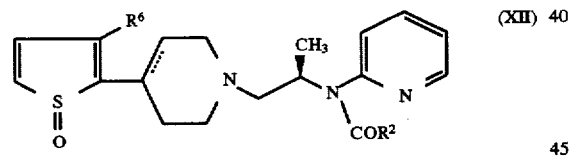 (XII)

and the pharmaceutically acceptable acid addition salts thereof.

In this class of compounds the thiophen-2-yl derivatives of formula (XI) are preferred. Particularly preferred compounds of the class are those in which R$^2$ is cycloalkyl, e.g. cyclohexyl. Examples of compounds of the class are:

(R)-[1-methyl-2-(4-thiophen-2-yl-1,2,3,6-tetrahydropyrid-1-yl)-ethyl]-pyrid-2-yl-amine, cyclohex-3-enecarboxylic acid (R)-[1-methyl-2-(4-thiophen-2-yl-1,2,3,6-tetrahydropyrid-1-yl)-ethyl]-pyrid-2-yl)-amide, or cyclohexanecarboxylic acid (R)-[1-methyl-2-(4-thiophen-2-yl-1,2,3,6-tetrahydropyrid-1-yl)-ethyl]-(pyrid-2-yl)-amide.

or a pharmaceutically acceptable acid addition salt thereof.

The compounds of the invention may be prepared by methods known in the art from known starting or starting materials that may be prepared by conventional methods. One method comprises acylating an amine of formula

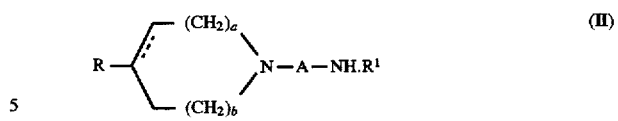 (II)

(where a, b, the dotted line, A, R and R$^1$ are as defined above) with an acid of formula

R$^2$COOH  (III)

or with an acylating derivative thereof. Examples of acylating derivatives include the acid halides (e.g. acid chlorides) azides, anhydrides, imidazolides (e.g. obtained from carbonyldiimidazole), activated esters or O-acyl ureas obtained from a carbodiimide such as a dialkylocarbodiimide particularly cyclohexyl-carbodiimide.

Some of the amines of formula II are novel and are also provided by the invention.

Particular novel compounds are those of the general formula

(where the dotted line and R$^6$ are as defined above), the sulphoxides thereof and the pharmaceutically acceptable acid addition salts thereof.

The amines of formula (II) may be prepared by methods known in the art (e.g. by reductive alkylation of the compound of formula IV below). A preferred method of preparing certain amines comprises reacting the compound of formula IV with, for example (R)-4-methyl-3-(pyrid-2-yl)-[1,2,3]-oxathiazolidine-2,2-dioxide Another method of preparing the compounds of formula I comprises alkylation of a compound of formula

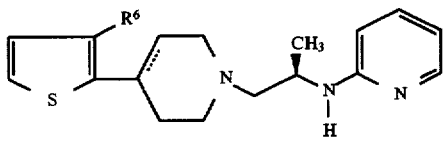 (IV)

(where R, a, b and the dotted line are as defined above) with an alkylating agent providing the group

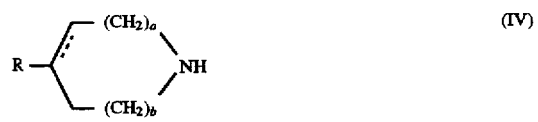 (V)

(where A, R$^1$ and R$^2$ have the meanings given above)

The alkylating agent may be, for example a compound of formula

 (VI)

where A, R$^1$ and R$^2$ are as defined above and X is a leaving group such as halogen or an alkyl- or aryl-sulphonyloxy group.

The alkylation of the compound of formula (IV) may also be carried out by reductive amination of the compound with a carbonyl compound of formula

(where $R^1$ and $R^2$ are as defined above and each $R^5$ is independently hydrogen or lower alkyl). The reductive amination may be carried out in the presence of a reducing agent such as $NaBH_3CN$ and $NaBH(OAc)_3$.

A further method of preparing the compounds of the invention comprises alkylating an amide of formula (VIII)

(where $R^1$ and $R^2$ are as defined above) with an alkylating agent providing the group

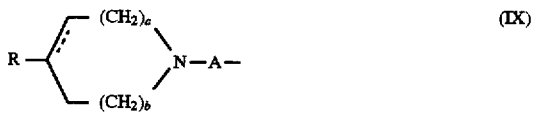

The alkylating agent may be, for example, a compound of formula

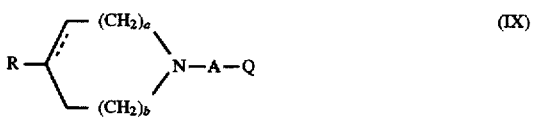

(where a, b, the dotted line, A and R are as defined above and Q is a leaving group such as a halogen (e.g. bromine) or an ester (e.g. a tosylate or trifluorosulphonate).

The compounds of formula (I) where the dotted line represents a double bond may be prepared by dehydrating a hydroxy amide of formula

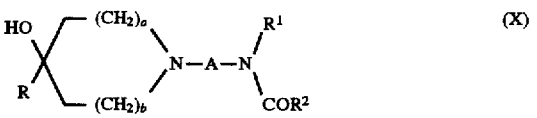

(where a, b, A, R, $R^1$ and $R^2$ have the meanings given above).

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention may contain one or more asymmetric carbon atoms, so that the compounds can exist in different stereoisomeric forms. All stereoisomeric forms are included within the invention. The compounds can be, for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors, particularly receptors of the 5-$HT_{1A}$ type. In general, the compounds selectively bind to receptors of the 5-$HT_{1A}$ type to a much greater extent than they bind to other receptors such as $\alpha_1$. The compounds can be used for the treatment of CNS disorders, such as anxiety in mammals, particularly humans. They may also be useful as antidepressants, antidementia agents, antipsychotics, hypotensives and as agents for regulating the sleep/wake cycle, feeding behaviour and/or sexual function.

The compounds of the invention are tested for 5-$HT_{1A}$ receptor binding activity in rat hippocampal membrane homogenate by the method of B. S. Alexander and M. D. Wood, J Pharm Pharmacol. 1988, 40, 888–891. In this procedure the compound of Example 1, a representative compound of the invention, had $IC_{50}$ values of 3.5 nM. The affinity for the $\alpha_1$ site (as measured by the procedure of A. L. Marrow et al, Mol Pharmacol. 1986, 29, 321) for the compound was $IC_{50}$=858 nM.

The compounds are tested for 5-$HT_{1A}$ receptor antagonism activity in a test involving the antagonism of 5-carboxamidotryptamine in the guinea-pig ileum in vitro (based upon the procedure of Fozard et al, Br J Pharmac, 1985, 86, 601 P). The above mentioned representative compound exhibits a $pA_2$ 7.9.

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention.

EXAMPLE 1

(R)-N-(2-(1-(4-(2-Methoxyphenyl)piperidinyl))propyl)-N-(2-pyridyl)cyclohexanecarboxamide To a solution of 2-(2-(1-(4-(2-methoxyphenyl)piperidinyl)propyl)amino)pyridine (570 mg, 1.75 mmol) in dry dichloromethane (20 ml) at 0° C., was added, with stirring under argon, cyclohexanecarbonyl chloride (0.246 ml, 1.84 mmol) followed by dry diisopropylethylamine (0.366 ml, 2.1 mmol). The reaction mixture was sealed from ingress of moisture and placed in a refrigerator for 36 hours. The completed reaction was diluted with dichloromethane and washed with saturated sodium chloride solution (10 ml). The organic layer was dried over $MgSO_4$, filtered and evaporated to an oil. The oil was purified by silica gel column chromatography to give the title compound (300 mg), m.p. 128° C.

Found: C, 74.36; H, 8.76; N, 9.39%. $C_{27}H_{37}N_3O_2$ requires: C, 74.45; H, 8.54; N, 9.63%.

EXAMPLE 2

(R)-N-(2-(1-(1,2,3,6-tetrahydro-4-(4-indolyl)-1-pyridyl))propyl)-N-(2-pyridyl)cyclohexanecarboxamide (a) Cyclohexanecarbonyl chloride (0.28 ml, 2.1 mmol) is added to a stirred ice cooled solution of (R)-2-(2-(1-(1,2,3,6-tetrahydro-4-(4-indolyl)pyrid-1-yl)propyl)amino)pyridine (650 mg, 2 mmol) in dichloromethane (25 ml), followed by diisopropylamine (0.45 ml). The reaction is allowed to stand overnight and washed with brine. The organic phase is separated, dried over $MgSO_4$, filtered and evaporated to give the title product which is purified by chromatography.

(b) (R)-N-(2-(1-(4-(indol-4-yl)piperidin-1-yl))propyl)-N-(2-pyridyl)cyclohexanecarboxamide The product from example 2(a) (0.5 g) is dissolved in ethanol (50 ml) and hydrogenated at atmospheric pressure over palladium (5% on carbon, 0.1 g) until uptake of hydrogen is complete. The solution is filtered, evaporated and the residue crystallised from ethanol to give the title compound.

EXAMPLE 3

(a) N-benzyl-4-hydroxy-4-(2,3-dihydrobenzo[1,4]dioxin-5-yl)piperidine

A toluene solution (10 ml) of 5-bromo-2,3-dihydrobenzo[1,4]dioxin (10 mmol) was stirred under argon at 0° C. and was treated with the dropwise addition of n-butyllithium (10 mmol) over ten minutes. After stirring for a further twenty minutes a solution of 1-benzyl-4-piperidone in toluene (10 mmol in 10 ml) was added dropwise over five minutes. Stirring was continued for two hours, at which point water (100 ml) was added and the product extracted into ethyl acetate (4×50 ml). The combined organics were washed with water (2×50 ml), brine (75 ml) and dried ($MgSO_4$). Filtration and concentration in vacuo gave an oil.

Purification by column chromatography ($SiO_2$, EtOAc) gave the required product in 61% yield.

(b) N-benzyl-4-(2,3-dihydrobenzo[1,4]dioxin-5-yl)-3,4,1,2,3,6-tetrahydropyridine A solution of N-benzyl-4-hydroxy-4-(2,3-dihydrobenzo[1,4]dioxin-5-yl)-piperidine (2.0 g) was dissolved in ethyl acetate (20 ml) and the solution treated with an excess of ethereal HCl. The salt precipitated immediately and was concentrated in vacuo. The solid was dissolved in glacial acetic acid (20 ml) and the solution was brought to a gentle reflux for 16 hours. The solvent was removed in vacuo, water (50 ml) added and the solution was made basic with 1N NaOH. The product was extracted into ethyl acetate (4×50 ml). The combined organics were washed with water (2×50 ml), brine (50 ml) and dried ($Na_2SO_4$). Filtration and concentration in vacuo gave the required product 2.0 g.

(c) 4-(2,3-dihydrobenzo[1,4]dioxin-5-yl)piperidine

A solution of N-benzyl-4-(2,3-dihydrobenzo[1,4]dioxin-5-yl)-1,2,3,6-tetrahydropyridine (1.9 g) in acetic acid (20 ml) was hydrogenated over Pearlman's catalyst (50 mg) at 50 psi and 50° C. for 24 hours. The product was isolated by filtration, concentration in vacuo, and neutralisation with aqueous KOH. It was used directly in the next step.

(d) (R)-2-{1-methyl-2-[4-(2,3-dihydrobenzo[1,4]dioxin-5-yl)piperidin-1-yl]propyl-ethyl}-aminopyridine A solution of 4-(2,3-dihydrobenzo[1,4]dioxin-5-yl)-piperidine (4.18 mmol) in acetonitrile (10 ml) was treated with (R)-4-methyl-3-(pyrid-2-yl)-[1,2,3]-oxathiazolidine-2,2-dioxide (4.18 mmol) and the solution was stirred under argon at ambient temperature for 16 hours. Hydrochloric acid (2N, 50 ml) was added and the mixture stirred for four hours, at which point the acetonitrile was removed in vacuo. The solution was neutralised with aqueous KOH and the product was extracted into ethyl acetate (3×100 ml). The combined organics were washed with water (100 ml), brine (100 mL) and dried ($MgSO_4$). Filtration and concentration in vacuo gave the product as a light oil. [74% yield].

(e) (R)-N-{1-methyl-2-[4-(2,3-dihydrobenzo[1,4]dioxin-5-yl)-piperdin-1-yl]ethyl}-N-(2-pyridyl)cyclohexanecarboxamide Triethylamine (6.16 mmol) was added to a solution of (R)-2-{1-methyl 2-[4-(2,3-dihydrobenzo[1,4]dioxin-5-yl)-piperidin-1-yl]-1-ethyl} amino pyridine (3.08 mmol) in dichloromethane (10 ml) under argon. After cooling to 0° C., cyclohexanecarbonyl chloride (3.08 mmol) was added and the reaction mixture was allowed to stir for 16 hours. The solvent was removed in vacuo, water (50 ml) was added, and the product was extracted into ethyl acetate (3×50 ml). The combined organics were washed with water (2×50 ml), brine (50 ml) and dried over anhydrous magnesium sulfate. Filtration and concentration in vacuo gave 1.35 gm of a light oil. The product was obtained as a white solid from an ethyl acetate/diethyl ether solvent mixture.

Found: C, 72.35; H, 8.03; N, 9.01% $C_{28}H_{37}N_3O_3$ Requires: C. 72.54; H, 8.04; N, 9.06%

$[\alpha]^{27}_D=-63°$.

The hydrochloride salt was formed by dissolving a sample of the compound in ethyl acetate and treating with excess ethereal HCl. The precipitated solid was collected and dried in vacuo.

MP 98° C. Found % C, 60.99; H, 7.71; N, 7.05 $C_{28}H_{37}N_3O_3.2HCl$. 0.5 $EtOAc.0.5H_2O$ Requires % C, 61.11; H, 7.52; N, 7.13 $[\alpha]^{26}_D=-56°$.

EXAMPLE 4

(R)-[1-Methyl-2-(4-thiophen-2-yl-1,2,3,6-tetrahydropyrid-1-yl)ethyl]-pyrid-2-yl-amine A mixture of 4-hydroxy-4-thiophen-2-yl-piperidine (3.3 g, 18 mmol) and (R)-4-methyl-3-(pyrid-2-yl)-[1,2,3]-oxathiazolidine-2,2-dioxide (3.7 g, 17.5 mmol) was stirred in dimethylformamide (70 ml) at ambient temperature for 40 minutes, then evaporated to dryness in vacuo and the residue dissolved in tetrahydrofuran (30 m) and water (10 ml). Concentrated sulfuric acid (2.9 g) was dropwise added while maintaining room temperature. Thereafter sodium hydrogencarbonate (6.7 g) were added in a portion wise fashion and the resulting suspension stirred at ambient temperature overnight. Water (100 ml) and ethylacetate (100 ml) were added to the reaction mixture and the pH adjusted to 10 with the addition of 0.5N NaOH. The product was extracted with ethylacetate (3×100 ml) and the combined organic layer washed with brine (150 ml), dried over magnesium sulfate, filtered, and evaporated to dryness. The obtained residue was dissolved in acetic acid (300 ml) and heated to 140° C. bath temperature for 3 hours. After cooling to room temperature the mixture was evaporated in vacuo and the residue partitioned between chloroform and 5% aqueous sodium hydrogencarbonate. The organic layer was separated, dried over magnesium sulfate, filtered, and evaporated in vacuo. Column chromatography on 120 g of silica gel with 2% methanol/ethylacetate as eluant, followed by trituration in ether with the addition of two molequivalent of fumaric acid gave 4.2 g of the title compound as the fumarate salt hemihydrate, m.p. 63°–8° C.

Elemental Analysis for: $C_{17}H_{21}N_3S.2C_4H_4O_4.0.5H_2O$. Calcd: C, 55.54; H, 5.59; N, 7.77. Found: C, 55.43; H, 5.48; N, 7.54.

EXAMPLE 5

Cyclohex-3-enecarboxylic acid (R)-[1-methyl-2-(4-thiophen-2-yl-1,2,3,6-tetrahydro-pyrid-1-yl)-ethyl]-(pyrid-2yl)-amide A solution of the starting (R)-[1-methyl-2-(4-thiophen-2-yl-3,6-dihydro-2H-pyrid-1-yl)-ethyl]-pyrid-2-yl-amine (0.46 g, 1.5 mmol) in methylene chloride (20 ml) was cooled to 0° C., after which a solution of cyclohex-3-enecarbonyl chloride (0.222 g, 1.5 mmol) in methylene chloride (10 ml) was dropwise added under exclusion of moisture. The reaction mixture was stirred at ambient temperature overnight, then washed with 2.5N NaOH (10 ml). The separated organic layer was washed with brine (50 ml), dried over magnesium sulfate, filtered, and evaporated to dryness in vacuo. Column chromatography on 50 g of silica gel with chloroform as eluant, followed by trituration in ether with the addition of ethanolic HCl gave 0.27g of the title compound as the dihydrochloride, m.p. 92°–6° C.

Elemental Analysis for: $C_{24}H_{29}N_3OS.2HCl$. Calcd: C, 59.99; H, 6.50; N, 8.74. Found: C, 59.75; H, 6.32; N, 8.39.

EXAMPLE 6

Cyclohexanecarboxylic acid (R)-[-1-methyl-2-(4-thiophen-2-yl-1,2,3,6-tetrahydropyrid-1-yl)-ethyl]-(pyrid-2-yl)-amide The title compound was prepared from (R)-[1-methyl-2-(4-thiophen-2-yl-3,6-dihydro-2H-pyrid-1-yl)-ethyl]-pyrid-2-yl-amine (2.4 g, 8 mmol) and cyclohexanecarbonyl chloride (1.173 g, 8 mmol) in the manner described in Example 5 above to yield 2.7 g of title compound as the dihydrochloride, m.p. 103°–6° C.

Elemental Analysis for: $C_{24}$ $H_{31}N_3OS.2HCl.0.75H_2O$. Calcd: C, 58.11; H, 7.01; N, 8.47. Found: C, 58.03; H, 7.04; N, 8.12.

EXAMPLE 7

Cyclohexanecarboxylic acid (R)-{1-methyl-2[4-(1-oxo-thiophen-2-yl)1,2,3,6-tetrahydropyrid-1-yl]-ethyl}-(pyrid-2-yl)-amide The title compound was prepared from cyclohexanecarboxylic acid (R)-[1-methyl-2-(4-thiophen-2-yl-3,6-dihydro-2H-pyrid-1-yl)-ethyl]-(pyrid-2-yl)-amide dihydrochloride (1.5 g, 3.6 mmol) and meta-chloroperbenzoic acid (0.632 g, 3.6 mmol) to yield 0.7 g of the title compound as the 1.8 hydrochloride, m.p. 109°–11° C.

Elemental Analysis for: $C_{24}$ $H_{31}N_3O_2S.1.8HCl$. Calcd: C. 58.68; H, 6.73; N, 8.55. Found: C, 58.23; H, 6.70; N, 8.19.

We claim:

1. A compound of the formula $$R-\underset{(CH_2)_b}{\overset{(CH_2)_a}{\bigg\langle}}\!\!\!\!\!\bigg\rangle N-A-N\underset{COR^2}{\overset{R^1}{\diagdown}} \quad (I)$$

or a pharmaceutically acceptable acid addition salt thereof, wherein a and b each represent 0, 1, 2 or 3 such that the sum of a+b is 0, 1, 2 or 3, the dotted line represents an optional double bond which may be present in the ring, provided that a is at least 1, A is an alkylene chain of 1 or 2 carbon atoms optionally substituted by one or more lower alkyl groups, R is aryl or heteroaryl, with the proviso that R is not an unsubstituted phenyl group, wherein aryl is phenyl or naphthyl each of which may be optionally substituted by one or more substituents independently selected from lower alkyl, lower alkenyl, lower alkynyl, lower alkoxy, hydroxy, halogen, haloloweralkyl, nitro, nitrile, aminocarbonyl, loweralkylaminocarbonyl, di-loweralkylaminocarbonyl, loweralkylcarbonyl, loweralkoxycarbonyl, amino, loweralkylamino, or di-loweralkylamino, and heteroaryl is a monocyclic aromatic heterocyclic ring having 5 to 7 ring members or a bicyclic aromatic heterocyclic ring system having 5 to 10 ring atoms, and, as heteroatoms in either such monocyclic ring or bicyclic ring system, one to three heteroatoms selected from N, S and O, said N atoms being non-bridging, including the sulphoxide of such a thiophenyl radical, and which may be optionally substituted as for aryl, or R is a bicyclic oxygen-containing aryl radical of the formula

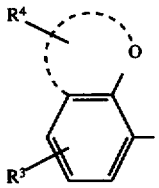

wherein the heterocyclic oxygen-containing ring has 5 to 7 ring members, said heterocyclic ring being saturated or unsaturated, but non-aromatic, and optionally having one further hetero ring member selected from —O—, —S—,—SO$_2$— or —NR$^5$—, where R$^5$ is hydrogen or lower alkyl, where R$^3$ and R$^4$ represent hydrogen or one or more substituents independently selected from lower alkyl, halogen, hydroxy, loweralkoxy, hydroxyloweralkyl, loweralkoxyloweralkyl, loweralkanoyloxy (loweralkyl), loweralkylcarbonyl, loweralkylcarbonyl-loweralkyl, loweralkylcarbonylamino, amino, loweralkylamino or di-loweralkylamino, R$^1$ is heteroaryl as defined for R, R$^2$ is cycloalkyl or cycloalkenyl of 3 to 12 carbon atoms;

wherein loweralkyl groups have 1 to 6 carbon atoms and lower alkenyl and loweralkyl groups have 2 to 6 carbon atoms.

2. A compound as claimed in claim 1 wherein the R heteroaryl moiety is selected from pyridinyl, pyrimidinyl, pyrazinyl, quinolinyl, isoquinolinyl, indolyl, benzisothiazolyl, thiophenyl or thiophenylsulphoxide.

3. A compound as claimed in claim 1 wherein the R heteroaryl moiety is selected from pyrimidinyl, indolyl, benzisothiazolyl, thiophenyl or thiophenylsulphoxide.

4. A compound as claimed in claim 1 wherein the R$^1$ heteroaryl moiety is selected from pyridinyl, pyrimidinyl, pyrazinyl, quinolinyl, isoquinolinyl, or indolyl.

5. A compound as claimed in claim 1 wherein

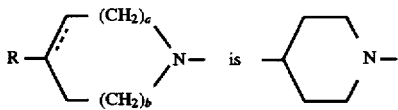

6. A compound as claimed in claim 1 wherein R is 2-(lower)alkoxyphenyl or an optionally substituted indolyl radical.

7. A compound as claimed in claim 1 in which A is —CH$_2$—, —CH$_2$CH$_2$— or —CH$_2$CH(CH$_3$)—.

8. A compound as claimed in claim 1 in which R$^1$ is 2-pyridyl.

9. A compound as claimed in claim 1 in which R$^2$ is cyclohexyl.

10. A compound as claimed in claim 1 of the formula

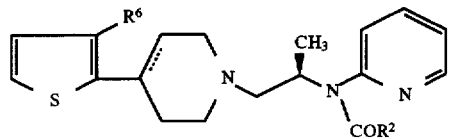

wherein the dotted line and R$^2$ are as defined in claim 1, R$^6$ is hydrogen, lower alkyl, lower alkenyl, lower alkynyl, nitrile, hydroxy, (lower)alkoxy, (lower)alkylcarbonyl, (lower)alkoxycarbonyl, carbamoyl, (lower)alkylcarbamoyl, di(lower)alkylcarbamoyl, halo(lower)alkyl or halogen or a sulphoxide thereof of formula

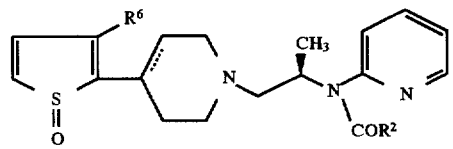

or a pharmaceutically acceptable acid addition salts thereof.

11. A compound as claimed in claim 1 which is:

(R)-N-(2-(1-(4-(2-methoxyphenyl)piperidino))propyl)-N-(2-pyridyl)cyclohexanecarboxamide, (R)-N-(2-(1-(4-(indol-4-yl)piperidin-1-yl))propyl)-N-(2-pyridyl)cyclohexanecarboxamide, (R)-N-{1-methyl-2-[4-(2,3-dihydrobenzo[1,4]dioxin-5-yl)-piperidin-1-yl]-ethyl}-N-(2-pyridyl) cyclohexanecarboxamide, (R)-[1-methyl-2-(4-thiophen-2-yl-1,2,3,6-tetrahydropyrid-1-yl)-ethyl]-pyrid-2-yl-amine, cyclohex-3-enecarboxylic acid (R)-[1-methyl-2-(4-thiophen-2-yl-1,2,3,6-tetrahydropyrid-1-yl)-ethyl]-(pyrid-2-yl)-amide, or cyclohexanecarboxylic acid (R)-[1-methyl-2-(4-thiophen-2-yl-1,2,3,6-tetrahydropyrid-1-yl)-ethyl]-(pyrid-2-yl)-amide or a pharmaceutically acceptable acid addition salt thereof.

12. A compound of formula

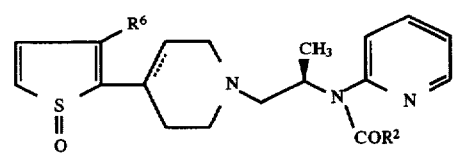

wherein the dotted line represents an optional double bond and R$^6$ is hydrogen, lower alkyl, lower alkenyl, lower alkynyl, nitrile, hydroxy, (lower)alkoxy, (lower) alkylcarbonyl, (lower)alkoxycarbonyl, carbamoyl, (lower) alkylcarbamoyl, di(lower)alkylcarbamoyl, halo(lower)alkyl or halogen.

13. A pharmaceutical composition comprising a compound claimed in claim 1 in association with a pharmaceutically acceptable carrier.

14. A method of treating a mammal suffering from a disease or a symptom susceptible to treatment by a 5-HT$_{1A}$ antagonism, comprising administering to such mammal an amount of a compound as claimed in claim 1 effective to provide 5-HT$_{1A}$ antagonism.

15. A process for preparing a compound claimed in claim 1, which comprises (a) acylating an amide of formula:

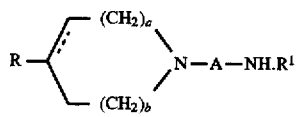
(II)

where a, b, the dotted line A, R and R¹ are as defined in claim 1 with an acid of formula $$R^2COOH \qquad (III)$$

or with an acylating derivative thereof or (b) alkylating a compound of formula:

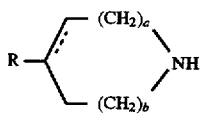
(IV)

(where R, a, b and the dotted line are as defined in claim 1) with an alkylating agent providing the group

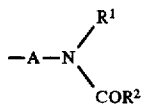
(V)

(where A, R¹ and R² have the meanings given in claim 1) or (c) alkylating an amide of formula (VIII)

(VIII)

(where R¹ and R² are as defined above) with an alkylating agent providing the group

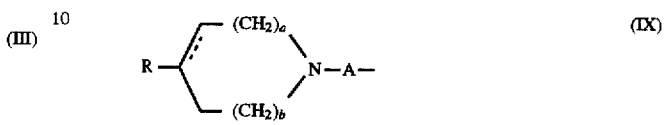
(IX)

or (d) dehydrating a hydroxy amide of formula

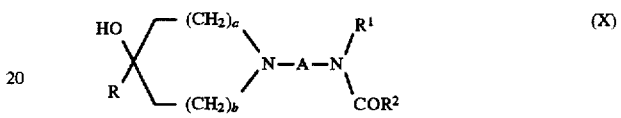
(X)

to give a formula (I) where the dotted line represents a double bond or (e) converting a base claimed in claim 1 into a pharmaceutically acceptable salt of converting a pharmaceutically acceptable salt into the free base.

* * * * *